United States Patent
Caluser

(10) Patent No.: US 9,439,624 B2
(45) Date of Patent: Sep. 13, 2016

(54) THREE DIMENSIONAL MAPPING DISPLAY SYSTEM FOR DIAGNOSTIC ULTRASOUND MACHINES AND METHOD

(75) Inventor: Calin Caluser, Glen Ellyn, IL (US)

(73) Assignee: Metritrack, Inc., Hillside, IL (US)

( * ) Notice: Subject to any disclaimer, the term of this patent is extended or adjusted under 35 U.S.C. 154(b) by 401 days.

(21) Appl. No.: 12/288,478

(22) Filed: Oct. 20, 2008

(65) Prior Publication Data

US 2009/0124906 A1 May 14, 2009

Related U.S. Application Data

(60) Provisional application No. 60/999,789, filed on Oct. 19, 2007.

(51) Int. Cl.
  *A61B 8/00* (2006.01)
  *A61B 5/06* (2006.01)
  *A61B 8/08* (2006.01)
  *G06F 19/00* (2011.01)

(52) U.S. Cl.
  CPC ............... *A61B 8/4263* (2013.01); *A61B 5/06* (2013.01); *A61B 8/00* (2013.01); *A61B 8/4245* (2013.01); *A61B 8/4254* (2013.01); *A61B 8/483* (2013.01); *G06F 19/321* (2013.01); *G06F 19/3406* (2013.01)

(58) Field of Classification Search
  USPC ........ 600/409, 420, 473, 424, 437; 382/128, 382/131, 132, 278, 282, 284
  See application file for complete search history.

(56) References Cited

U.S. PATENT DOCUMENTS

| 5,438,996 | A | 8/1995 | Kemper et al. |
| 5,911,126 | A | 6/1999 | Massen |
| 6,171,244 | B1 | 1/2001 | Finger et al. |
| 6,203,497 | B1 * | 3/2001 | Dekel et al. ................. 600/439 |

(Continued)

FOREIGN PATENT DOCUMENTS

| WO | 2004098414 A1 | 11/2004 |
| WO | WO 2005/099581 | * 10/2005 |
| WO | WO 2006008300 A1 | 1/2006 |

OTHER PUBLICATIONS

Pagoulatos et al., "Interactive 3-D registration of ultrasound and magnetic resonance images based on a magnetic position sensor", IEEE Transactions on Information Technology in Biomedicine, vol. 3, pp. 278-288, Dec. 1999.*

*Primary Examiner* — Amanda Lauritzen Moher
*Assistant Examiner* — Shahdeep Mohammed
(74) *Attorney, Agent, or Firm* — Ziolkowski Patent Solutions Group, SC

(57) ABSTRACT

An apparatus, system, and method where the ultrasound transducer position registration is automated, calculates the position of each pixel in the ultrasound image in reference to the predetermined anatomical reference points (AR) and can store the information on demand. The graphic interface associated with the ultrasound image allows for the instant display of selected targets position coordinates relative to anatomical reference points, in the ultrasound images. This system would significantly reduce the ultrasound examination time, by eliminating the time consuming manual labeling of images and speeding up the target finding at subsequent examinations, enhance correlation capability with other diagnostic imaging modalities like CT scans, MRI, mammograms, decrease human errors and fatigue, provide an easy, uniform, method of communicating the target position among healthcare providers.

16 Claims, 8 Drawing Sheets

(56) References Cited

U.S. PATENT DOCUMENTS

| | | |
|---|---|---|
| 6,261,247 B1 | 7/2001 | Ishikawa et al. |
| 6,390,982 B1* | 5/2002 | Bova et al. ............... 600/443 |
| 6,443,894 B1* | 9/2002 | Sumanaweera et al. ..... 600/443 |
| 6,500,118 B1 | 12/2002 | Hashimoto |
| 6,669,653 B2 | 12/2003 | Paltieli |
| 6,675,038 B2 | 1/2004 | Cupples et al. |
| 7,176,916 B2 | 2/2007 | Riaz |
| 7,220,955 B2 | 5/2007 | Brunfeld et al. |
| 7,229,411 B2 | 6/2007 | Slayton et al. |
| 7,238,158 B2 | 7/2007 | Abend |
| 7,244,230 B2 | 7/2007 | Duggirala et al. |
| 7,251,352 B2 | 7/2007 | Sauer et al. |
| 7,255,695 B2 | 8/2007 | Falwell et al. |
| 7,259,897 B2 | 8/2007 | Garlick et al. |
| 7,260,426 B2 | 8/2007 | Schweikard et al. |
| 7,639,895 B2* | 12/2009 | Sakas et al. ............... 382/284 |
| 2002/0049375 A1* | 4/2002 | Strommer et al. ............ 600/407 |
| 2004/0019274 A1 | 1/2004 | Galloway, Jr. et al. |
| 2004/0106869 A1 | 6/2004 | Tepper |
| 2005/0119569 A1 | 6/2005 | Ohtake |
| 2005/0251028 A1* | 11/2005 | Boese et al. ............... 600/425 |
| 2006/0020204 A1 | 1/2006 | Serra et al. |
| 2006/0241445 A1 | 10/2006 | Altmann et al. |
| 2006/0247918 A1 | 11/2006 | Schmidt et al. |
| 2007/0010743 A1 | 1/2007 | Arai |
| 2007/0023671 A1 | 2/2007 | Britten |
| 2007/0083117 A1* | 4/2007 | Sakas et al. ............... 600/437 |
| 2007/0167805 A1 | 7/2007 | Clement |
| 2007/0239004 A1* | 10/2007 | Kakee et al. ............... 600/437 |
| 2008/0085042 A1* | 4/2008 | Trofimov et al. ............. 382/128 |
| 2008/0095421 A1* | 4/2008 | Sun et al. ................... 382/131 |
| 2008/0200808 A1* | 8/2008 | Leidel et al. ............... 600/443 |
| 2008/0221446 A1* | 9/2008 | Washburn et al. ........... 600/437 |
| 2008/0262338 A1* | 10/2008 | Paitel et al. ................ 600/409 |

* cited by examiner

THREE DIMENSIONAL MAPPING DISPLAY SYSTEM FOR DIAGNOSTIC ULTRASOUND MACHINES AND METHOD

PRIORITY CLAIM

This application claims the priority of provisional application No. 60/999,789 filed Oct. 19, 2007.

COMPUTER PROGRAM

Incorporation by Reference

This Specification incorporates by reference the material contained on the enclosed compact disc (Appendix A) that includes the source code of the computer program for use with the inventive apparatus. The submission comprises a single compact disc, submitted in duplicate (labeled Copy 1 and Copy 2 and identical in content), created on Oct. 18, 2008 from files created Oct. 14, 2008, entitled Three Dimensional Mapping Display System for Diagnostic Ultrasound Machines and Method and containing the following files:

| File | Size |
| --- | --- |
| CapturePCIBird | 4.87 kb |
| DShowNET | 81.60 kb |
| FileBirdNETApi | 17.30 kb |
| FileBirdNETApiProvider | 9.68 kb |
| Math3D | 23.30 kb |
| MSSQLDBStorageProvider | 7.74 kb |
| MTMDController | 288.00 kb |
| MTMDDatabaseManager | 71.80 kb |
| MTMDFakeVideoCaptureProvider | 3.44 kb |
| MTMDPostgreDBStorageProvider | 10.90 kb |
| MTMDVideoCaptureCardProvider | 38.90 kb |
| MTMDWindowDisplayProvider | 21.10 kb |
| NetBirdApiProvider | 205.00 kb |
| NETBirdCommon | 30.90 kb |
| PCIBirdNET | 25.40 kb |
| PCINetBirdProvider | 5.58 kb |
| TestPCIBird | 58.70 kb |
| WildCard.Database | 15.00 kb |
| Total Size on Disk | 1,067.00 kb |

TECHNICAL FIELD

The present invention relates to diagnostic ultrasound technology and, more particularly, to a diagnostic ultrasound system in which ultrasound probe position registration is automated, the position of each pixel in the ultrasound image in reference to predetermined anatomical reference points is calculated, and specified information is stored on command. Moreover, the system, during real time ultrasound scanning enables the ultrasound probe position and orientation to be continuously displayed over a body or body part diagram, thereby facilitating the storage of information.

BACKGROUND OF THE INVENTION

Ultrasound is an important imaging modality for medical diagnostic purposes and as a guidance tool for diagnostic or therapeutic procedures, like soft tissue needle biopsy, tumor ablation, etc. Ultrasound can be used over the entire human body and has certain advantages over other modalities, including, among others: the ability to locate and characterize medical problems; lower cost compared to modalities such as MRI and CT; real time operation; and, the lack of ionizing radiation with the known associated health risks.

Ultrasound imaging systems transmit sound waves of very high frequency (e.g., 1 MHz to 20 MHz) into the patient's body and the echoes scattered from structures in the patient's body are processed to create and display images and information related to these structures.

Ultrasound imaging can be applied to various regions or organs in the body. For example, a breast ultrasound procedure involves the placement of an ultrasound transducer over a region of interest of the breast, with the radiologist or other medical professional (the "user") viewing a real-time ultrasound image output on a display. The ultrasound machine monitor usually displays relevant text and/or graphical information next to the ultrasound image for simultaneous viewing by the user. The user can freeze the display, and the corresponding image can be printed on a printer or stored in digital format.

Two dimensional ("2D") ultrasound imaging, the most common technique used today, represents a slice through the region of interest. Three-dimensional ("3D") ultrasound scanning is available; however, it is usually used in conjunction with 2D scanning techniques. Currently, most diagnostic studies are performed using 2 D scanning technique.

The vast majority of ultrasound guided biopsies and other invasive ultrasound guided invasive procedures done by free hand and other more automated modes use the ultrasound machine 2D display mode. Therefore, it is desirable to have a fast and accurate way to find the target during such invasive procedures.

It is important to accurately store positional annotations for later evaluation, since this is essential for final interpretation, diagnosis, and treatment. As digital storage and communication of medical information replace hard copy based storage and communication technologies, the accurate and consistent annotation of ultrasound and other medical images is critical. Correlation of ultrasound images with images of the same body region obtained with other modalities (MRI, CT, mammograms, PET, etc.) becomes increasingly important for medical diagnostic and therapeutic purposes. As a result, precise positional registration of the targets is important.

This importance is illustrated by noting that finding a small tumor can save a patient's life. The smaller the tumor is before treatment, the higher the probability of long term patient survival; however, a small tumor is difficult to find in a patient's body and differentiate from other structures in the same region. Many times a suspicious small finding can coexist in the same region with multiple benign findings (cysts, solid benign nodules, etc), which may create confusion during a follow up exam and may lead to missing the suspicious lesion. As imaging diagnostic devices provide ever greater detail and sub-millimeter resolution, accurate position registration and mapping of lesions is becoming increasingly important in order to take advantage of the increased capabilities.

Ultrasound procedures are highly dependent on the device user's experience and training. Position recording of certain findings is important, especially for the small targets and/or multiple targets. Most frequently, an ultrasound user will hold the ultrasound transducer in one hand and use the other hand to operate the ultrasound machine controls. It is desirable to obtain the instant recording of target coordinates seen in the ultrasound image in relation to the anatomical reference (for example, a nipple) and the simultaneous recording of the transducer position. Currently, the automated recording of the transducer position in real time scanning is limited due to the motion of the pre-selected anatomical reference secondary to body and transducer induced motion. Therefore, it is desirable to continuously update the position of the anatomical references, or landmarks, and apply the correction to the obtained measurements.

The American College of Radiology (ACR) recommends that all ultrasound images be properly labeled. For example, for breast ultrasound images, the position, in hourly format or other format, and distance from nipple should be displayed with each diagnostic image containing significant findings. Currently, ultrasound findings are manually labeled by an operator, which is time consuming and prone to errors. Manual labeling involves the typing of an approximate position in the organ or part of the body, since an accurate position registration is time consuming and, importantly, difficult for the user.

Although multiple ultrasound guidance systems and devices already exist, they do not offer a practical and accurate solution to mapping patient findings in 2D or 3D images in relation to set anatomical reference point(s), which is operator independent during a routine examination, with real time correction for the patient's motion. It would be beneficial, therefore, to obtain the accurate position of selected targets in the ultrasound images in relation to set anatomical reference point(s) with the corresponding ultrasound transducer position and orientation by selecting the target in the ultrasound image at the time of examination or at a later date in the stored images with attached positional information. The present invention provides such an advance to the art.

Objects and Advantages of the Present Invention

Copyright & Legal Notice

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

It is an object of the present invention to significantly reduce the time of the examination by eliminating the time consuming manual labeling of images and speeding up the target finding at subsequent examinations.

It is a further object of the present invention to obtain the accurate position of selected targets in ultrasound images in relation to set anatomical reference point(s) with the corresponding ultrasound transducer position and orientation by selecting the target in the ultrasound image at the time of examination or at a later date in the stored images with attached positional information in both 2D or 3D imaging techniques.

It is a further object of the present invention to enhance correlation capability with other diagnostic imaging modalities like CT scans, MRI, mammograms etc.

It is yet a further object of the present invention to eliminate or minimize errors due to inaccurate position labeling, therefore reducing the risk of costly lawsuits due to missed diagnosis and decrease the number of callbacks for the patients for repeat examination.

One advantage, among the many that will be appreciated by those skilled in the arts, is that the present invention provides an easy, uniform, method of communicating the target position among healthcare providers by guiding the ultrasound to a previously recorded target through following the real time display of the ultrasound transducer position in relation to the target coordinates from a previous examination.

SUMMARY OF THE INVENTION

The present invention provides an apparatus and method of use for automated ultrasound probe position registration, calculating the position of each pixel in the ultrasound image in reference to the predetermined anatomical reference points (AR), and storing selected information on demand. The present invention further enables, during real time ultrasound scanning, continuous ultrasound probe position and orientation display, which display be permanently stored in the system's memory at the users command.

The Present invention comprises a hardware/software application and real time commercial 3D position registration system interfaced with an ultrasound machine.

After initial calibration and selection of one or more anatomical reference (nipple, umbilicus etc), positional information associated with each individually recorded image frame or each image in a cine loop is stored with the corresponding image. Using a pointing device with the system display, spatial numerical coordinates of the selected pixel or region, including the distance from the anatomical reference, depth, angle to the body axis and a graphical representation, are displayed next to the ultrasound image. Also displayed are the real time position of the ultrasound probe and target position in a diagram shown next to the real time ultrasound image, providing orientation help for the ultrasound operator.

Each ultrasound saved image or set of images in a cine loop will have attached the positional information corresponding to each pixel in the ultrasound frame and the diagram with the body part with the ultrasound transducer position and orientation in reference to the anatomical reference(s) and position of a target pixel(s), if any are selected. Other body parts or regions can be recorded with corresponding anatomical reference points, ex.: liver with umbilicus, neck with thyroid cartilage etc. Target pixel selection can be made at the time of the image capture, before saving the image, or at a later time at the review station.

During future examinations, the user is guided to the target by entering the target coordinates obtained at the previous examination, display the target in the body diagram and adjust the transducer position in the real time body diagram to overlap the target.

For the accurate automated recording of body targets and transducer position related to certain anatomical references, a user continuously obtains positional information from the preset anatomical references and the motion correction instantly applied to the transducer positional coordinates.

This is achieved by continuously monitoring the preset anatomical reference point(s) position, which in the preferred embodiment can be achieved with a magnetic sensor placed next to the anatomical reference on the skin. In an alternate embodiment the anatomical reference tracking can be obtained with an overhead tracking system using digital infrared or optical cameras with or without skin markers. In this embodiment, one camera can be used, or two or more cameras can be also used to achieve a three dimensional stereoscopic effect.

There has been outlined, rather broadly, the more important features of the invention in order that the detailed description thereof that follows may be better understood, and in order that the present contribution to the art may be better appreciated. There are, of course, additional features of the invention that will be described hereinafter and that will form the subject matter of the invention.

DETAILED DESCRIPTION OF THE PREFERRED EMBODIMENT

Before explaining the preferred embodiment of the present invention in detail, it is to be understood that the present invention is not limited in its application to the details of arrangements of the components set forth in the following description. As will be appreciated by those skilled in the arts, the present invention is capable of other embodiments and of being practiced and carried out in various ways. Also, it is to be understood that the phraseology and terminology employed herein are for the purpose of description and should not be regarded as limiting. It is also to be understood that where ranges are provided for various aspects of the invention and for examples, they are approximate ranges and are not to be limiting except where noted otherwise.

Figure 1:
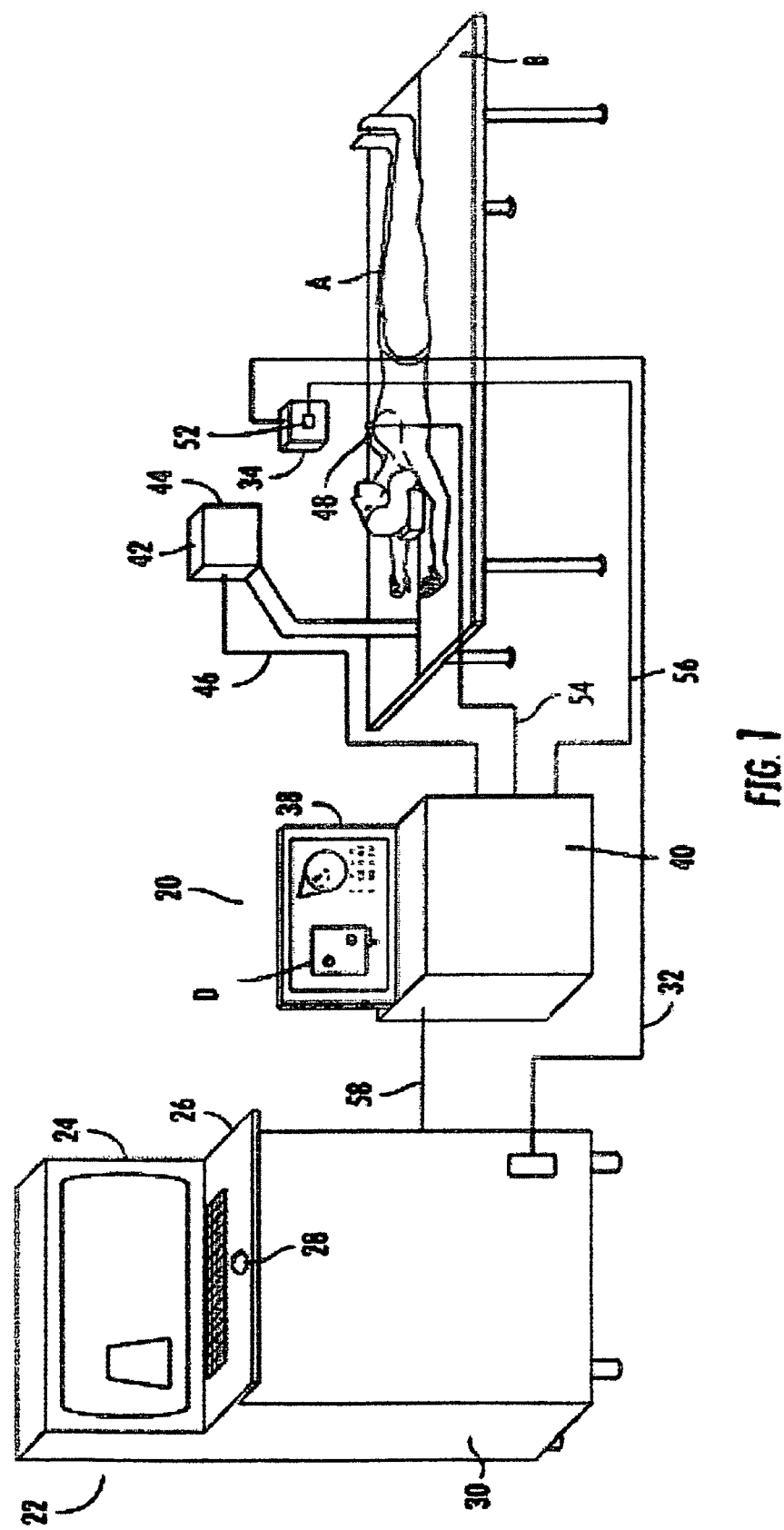
FIG. 1 depicts an overview illustration of the inventive apparatus placed in an ultrasound system.

Turning to FIG. 1, an over view of the physical aspects of an ultrasound device employing the inventive apparatus 20 is seen. Ultrasound machine 22 is a standard device including display 24, interface with keyboard 26 and pointer 28, chassis containing operating hardware (not seen) 30, transducer connecting cord 32, and transducer 34.

Inventive apparatus (also referred to as three dimensional mapping display, or TDMD) 20 is depicted and comprises TDMD display 38, TDMD Chassis 40 containing hardware (also referred to as a "processor") and software (not seen; described in detail below), 3D magnetic tracking member 42 with the transmitter 44 connected to TDMD 20 by 3D magnetic tracking member cord 46, first magnetic sensor 48 connected to TDMD 20 by first magnetic sensor cord 54 and second magnetic sensor 52 connected to TDMD 20 by second magnetic sensor cord 56.

For completeness in explaining FIG. 1, Patient A is situated on examining table B.

Figure 2:
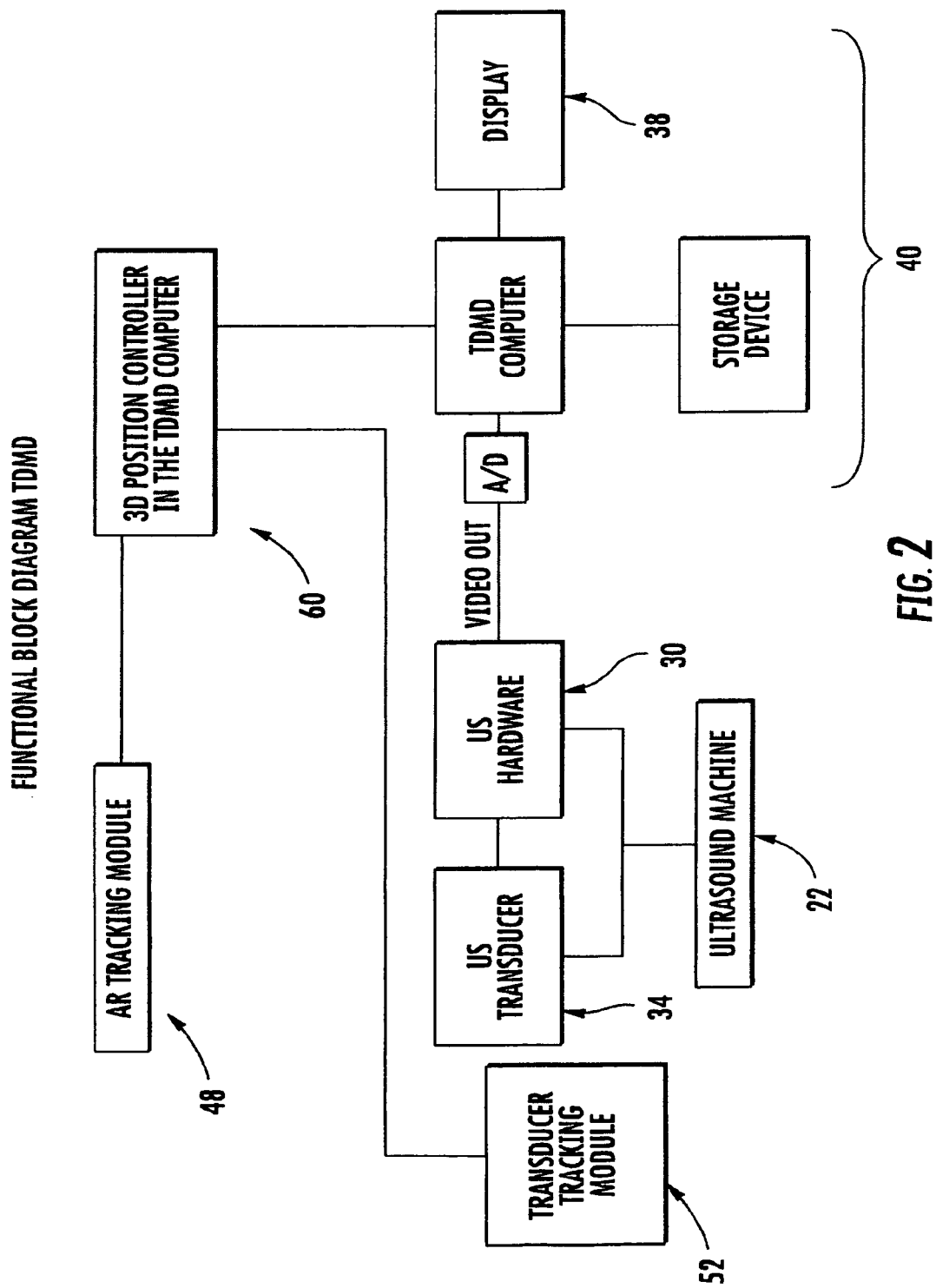
FIG. 2 illustrates the functional block diagram for the inventive device preferred embodiment with a magnetic sensor used for anatomical reference tracking.

Turning to FIG. 2, a block diagram illustrating the various general working aspects of inventive device 20 are shown. First magnetic sensor 48 and second magnetic sensor 52 provide the positional information to the TDMD 20 3D position board/module 60 (not seen). Video output 24 from ultrasound device 22 is digitized by the dedicated TDMD module/board 40. It should be noted that the analog to digital image conversion is not needed if the ultrasound machine can be interfaced and it can directly provide the digital images to the TDMD 22.

TDMD can continuously track one or several anatomical reference markers or positional body markers, which can increase the overall accuracy of the system. If multiple positional body markers are used, not all of them need to be continuously tracked. The positional body markers may be surface markers, attached at the skin, or may be internal markers, endocavitary, endoluminal or otherwise placed in the body at a known position. A known internal structure, like vessel crossing, may also serve as an anatomical reference point but without the advantage of having the position continuously tracked.

Figure 3:
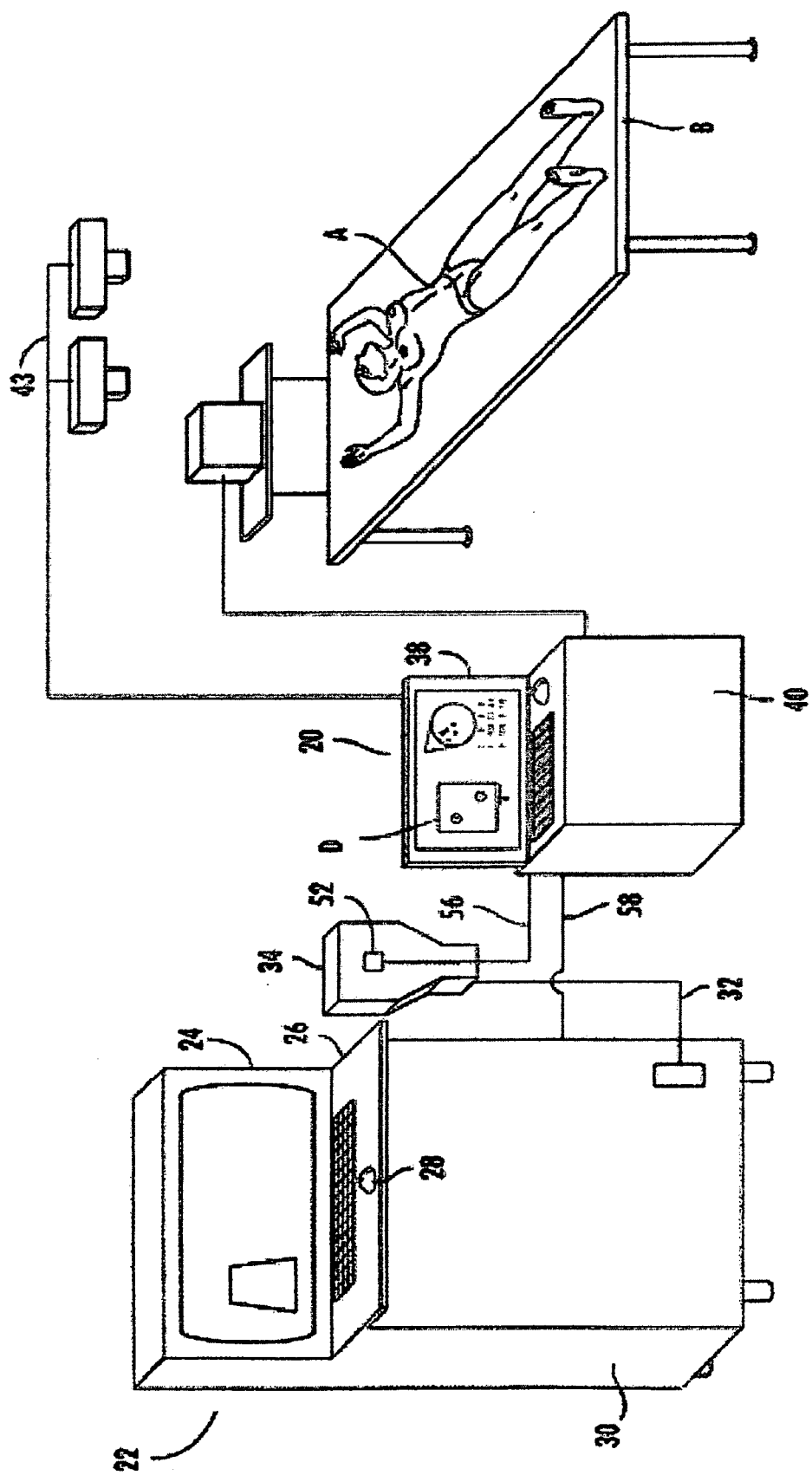
FIG. 3 depicts an alternate embodiment illustrating an overhead infrared or optical anatomical reference tracking system.

Other configurations will work as well. For non-limiting example, FIG. 3 illustrates an alternate configuration in which second magnetic sensor 52 provides the positional information to the TDMD 3D position board/module 60. The overhead infrared or optical anatomical reference (AR) tracking system 43 provides the positional information to the TDMD computer 40. Video output 24 from the ultrasound device 22 is digitized by the dedicated TDMD module/board 40. Again, analog to digital image conversion is not required if the ultrasound device 22 can be interfaced and directly provide the digital images to TDMD computer 40. The digital ultrasound images with the associated positional information are displayed in the TDMD computer display 38 or stored for review and processing at a later time.

Figure 4:
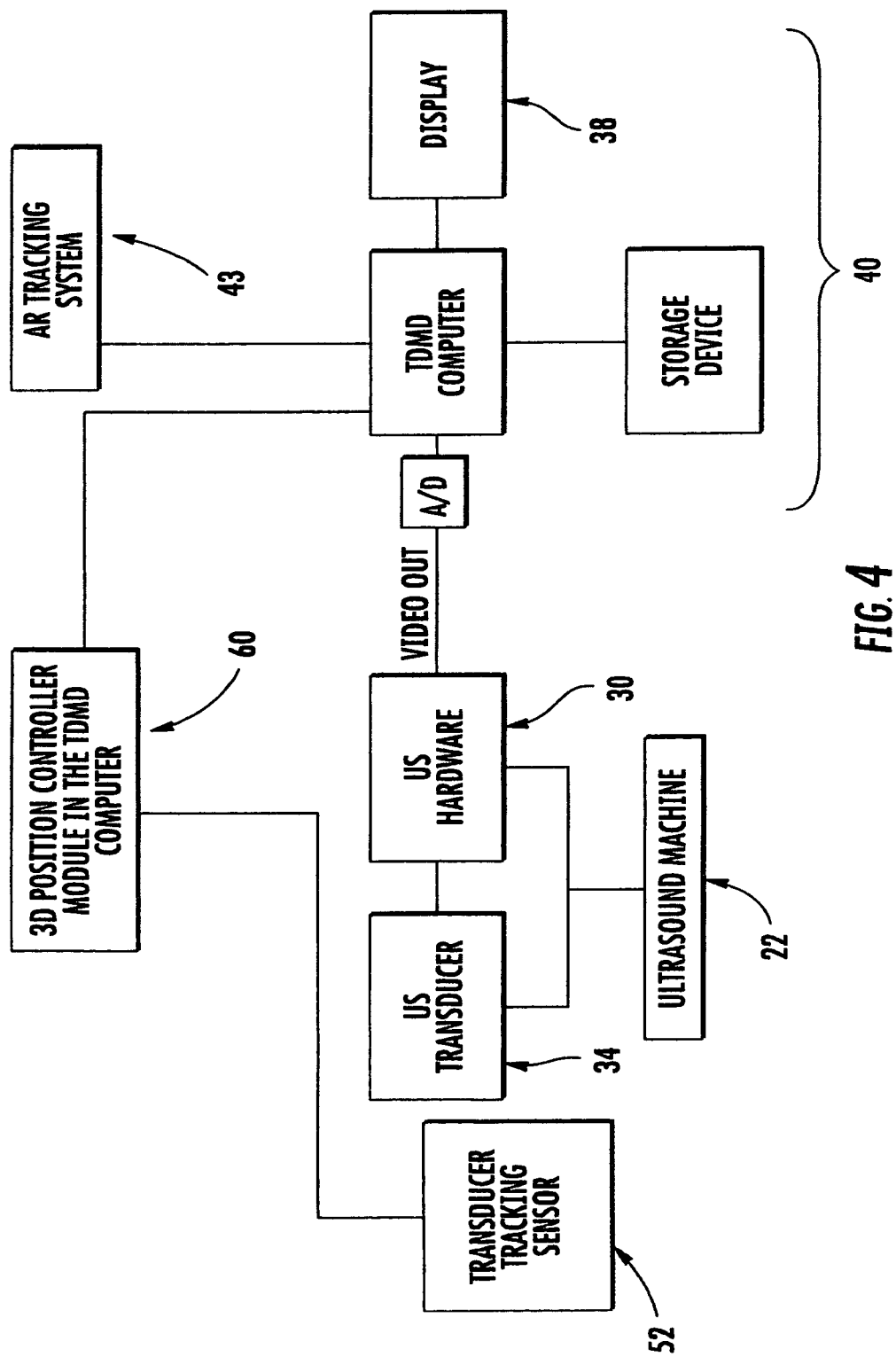
FIG. 4 illustrates the functional block diagram for the inventive device in the alternate embodiment with an overhead infrared or optical anatomical reference tracking system.

Turning to FIG. 4, a block diagram illustrating the various general working aspects of inventive device 20 are shown. Second magnetic sensor 52 provides the positional information to the TDMD 20 3D position board/module 60 and overhead infrared position detector 43 transmits positional information to TDMD computer 40. Video output 24 from ultrasound device 22 is digitized by the dedicated TDMD module/board 40. It should be noted that the analog to digital image conversion is not needed if the ultrasound machine can be interfaced and it can directly provide the digital images to the TDMD 22.

Figure 5:
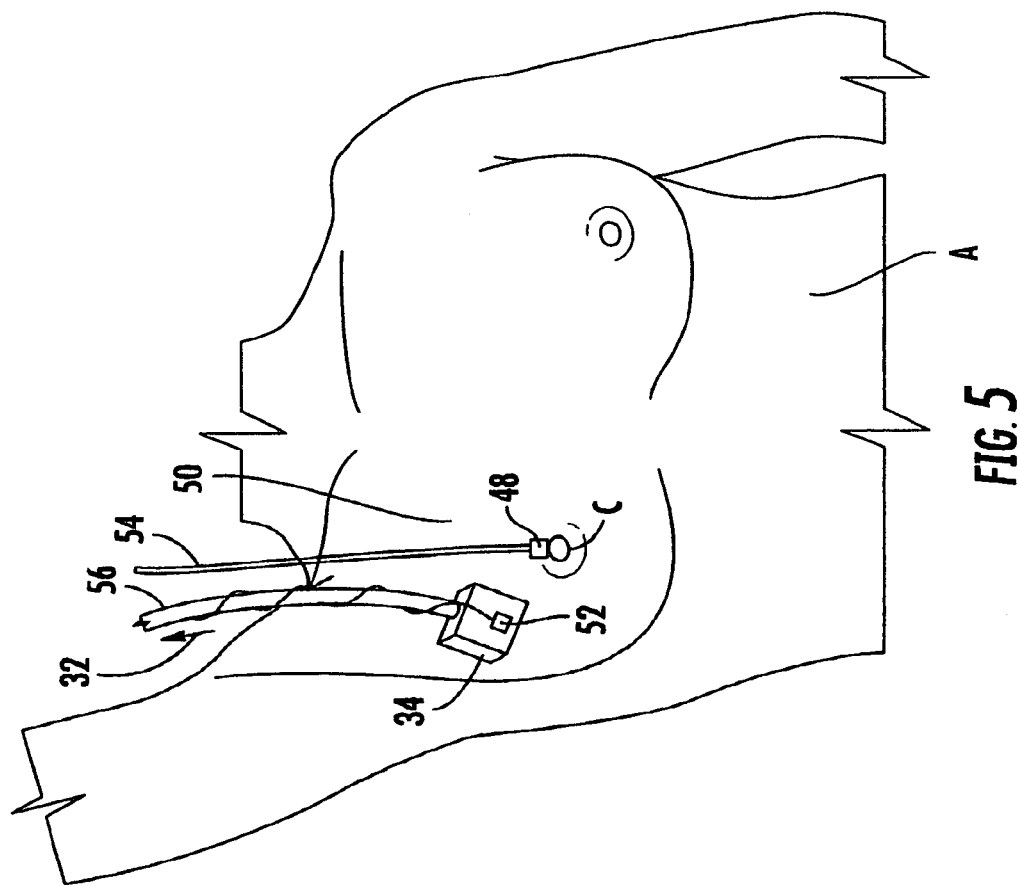
FIG. 5 depicts the inventive apparatus in a breast ultrasound examination

Returning to FIG. 1, second magnetic sensor 52 is attached to the exterior of transducer 34 and, as seen in more detail in FIG. 5, first magnetic sensor 48 is positioned at the anatomical reference, here, the breast nipple C of Patient A.

Ultrasound device 22 video output 24 is directed to TDMD video capture board at TMDS Chassis 40 through video output cord 58 as is 3D magnetic tracking member 42 through 3D magnetic tracking member cord 46. TDMS display 38 is then enabled to shows images D captured by ultrasound device 22 and associated positional data as collected from 3D tracking member 42, first magnetic sensor 48 and second magnetic sensor 52.

Figure 6:
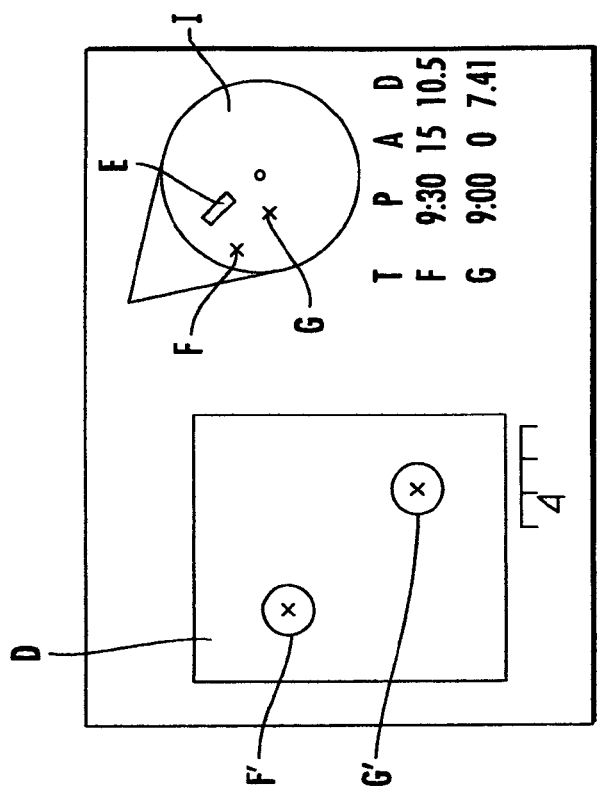
FIG. 6 depicts the image created during a breast examination as illustrated in FIG. 5.

Turning to FIG. 5, a detailed view of transducer 34 with the second magnetic sensor 52 and first magnetic sensor 48 applied at the upper margin of the right nipple. First magnetic sensor 48 continuously tracks the anatomical reference position, the nipple in this case, to compensate for motion artifacts during the ultrasound exam. FIG. 6 illustrates TDMD display 38 with the captured video image D from the ultrasound machine and the body diagram of FIG. 5 with the transducer 34 position and orientation at the time of image capture D and two different targets F and G in body part diagram I, and F' and G' as selected in image D image capture.

Additionally, each target is displayed with the associated position (hourly representation or degrees to longitudinal axis and anatomical reference as center) and distance (cm) from the selected anatomical reference F and G. Positional coordinates are displayed under body part diagram I in FIG. 6. While the inventive device enable any number of coordinates to be displayed, here the example includes Target number (T), example F and G, Positional in reference to anatomical reference in hour format (here, 9:30 for F and 9:00 for G), position from anatomical reference point in degrees (here, 15° for F and 0° for G), and distance from anatomical reference point in centimeters (cm) (here, 10.5 cm for F and 7.41 cm for G). Also, transducer 34 position location is identified at transducer position Icon E.

Additionally, an additional display function is to show a cumulative area of the transducer positions (via icon E) over the body diagram, where the ultrasound images were recorded during patient examination. This will allow for the quick evaluation of an ultrasound examination completeness, at the time of the examination or at a later time.

In the preferred embodiment, any off the shelf generic PC computer with Windows XP® (by Microsoft Corporation, Redmond, Wash.) can be used to run instructions compiled in C++ and dotnet languages. While preferred, those skilled in the arts will understand that the invention can be implemented on any other computer platform and operating system.

The software to run the program is that incorporated by reference above. The software substantially used to process the data received by the processor form the at least one sensor and data from the ultrasound to manipulate the data for identifying, and storing in memory as selected by the user, target site location and size information in relation to selected anatomical reference points for simultaneous review and interpretation and later retrieval for comparative purposes with later examination, whether compared in real time or a later time based upon saved data. The inventive device enabling a user to accurately review, evaluate, and compare examination results by having anatomical reference point guides to isolate target sites.

The body diagram representation is not limited to the "bird's eye view" type like the "clock" representation for the breast, but more complex and realistic three dimensional representations of the body or body regions, including images obtained using contour rendering algorithms, can be used. The calculated and recorded positional data can be displayed in these representations. The ultrasound transducer position, orientation, can be depicted in a realistic appearance in space so it can be easily reproduced at subsequent examinations.

Additionally, the preferred 3D position registration system is based on magnetic tracking technology (for example, like that manufactured by Ascension Technology, Burlington, Vt.); however, any other suitable technology, such as optical or ultrasound, may be employed. Moreover, the inventive device can be deployed as an add on to any existing ultrasound unit, and can outfit DICOM compatible and non DICOM machines as well. The magnetic sensors, also commercially available (Natural Point inc., Corvallis, Oreg.), comprise at least one infrared cameras with the dedicated hardware and software receiving reflected infrared light from the reflectors applied over the anatomical references. The infrared cameras can be replaced with optical cameras and the infrared reflectors with optical markers. One or more infrared or optical cameras can also be used.

The ultrasound probe and anatomical reference point real time tracking is not limited to the above solution, but other tracking modalities like ultrasound, optical, inertial etc. can be used for the ultrasound probe and optical/pattern recognition, magnetic, etc. for the anatomical reference point real time tracking. It should also be noted that tracking modalities can be used in combination with one another, for non-limiting example, ultrasound tracking with optical tracking. It is also notable that the described TDMD system and method can optionally be used with the anatomical reference tracking feature disabled.

Figure 7:
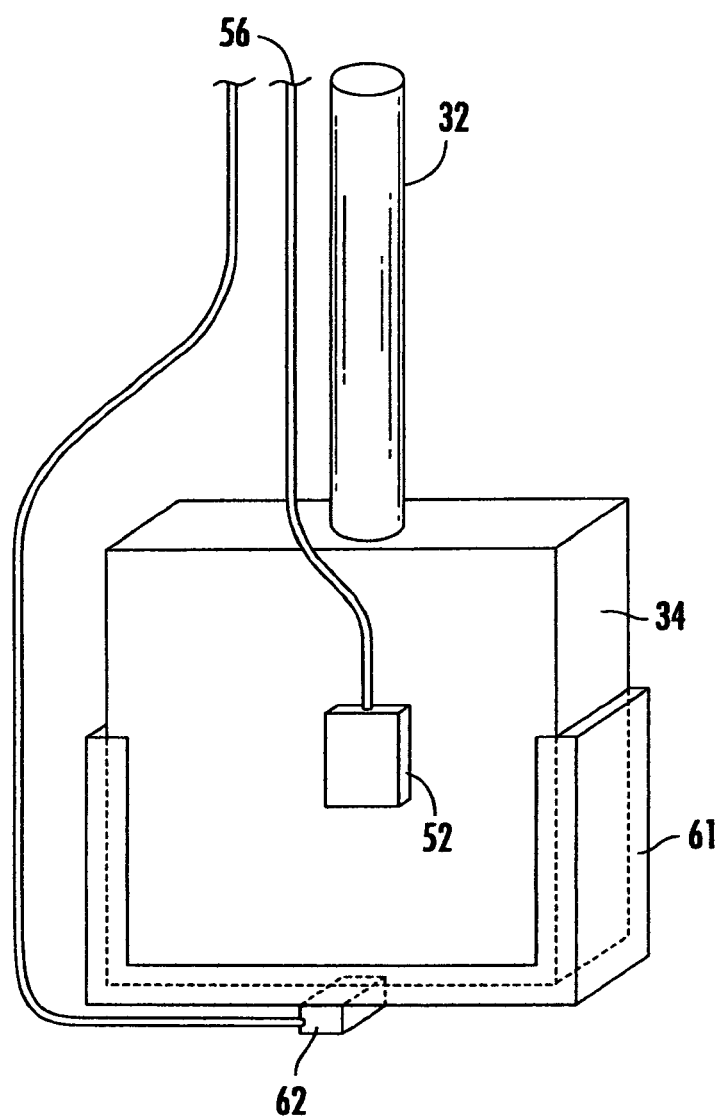
FIG. 7 illustrates the ultrasound transducer with the sensors in the calibrating tool.

In any of the above configurations, initial calibration is needed to register the ultrasound probe scanning plane orientation and position. The initial calibration may be performed with or without the use of a second positional sensor 62 (FIG. 7), however the use of a second magnetic sensor makes the calibration task easier and more precise. Without second positional sensor 62, scanhead center of transducer 34 and plane orientation need to be manually entered. This initial calibration is done once only, unless a different ultrasound probe is used or the fixed magnetic sensor position on the ultrasound transducer is modified. As those skilled in the arts will understand, there are many ways and methods to calibrate ultrasound equipment. For non-limiting example, one method includes placing ultrasound transducer 34 in a dedicated holder 61 which has the calibrating magnetic sensor 62 attached to correspond exactly to the center of the ultrasound transducer 34 scanning head, in a position aligned with the scanning plane of the transducer.

Figure 8:
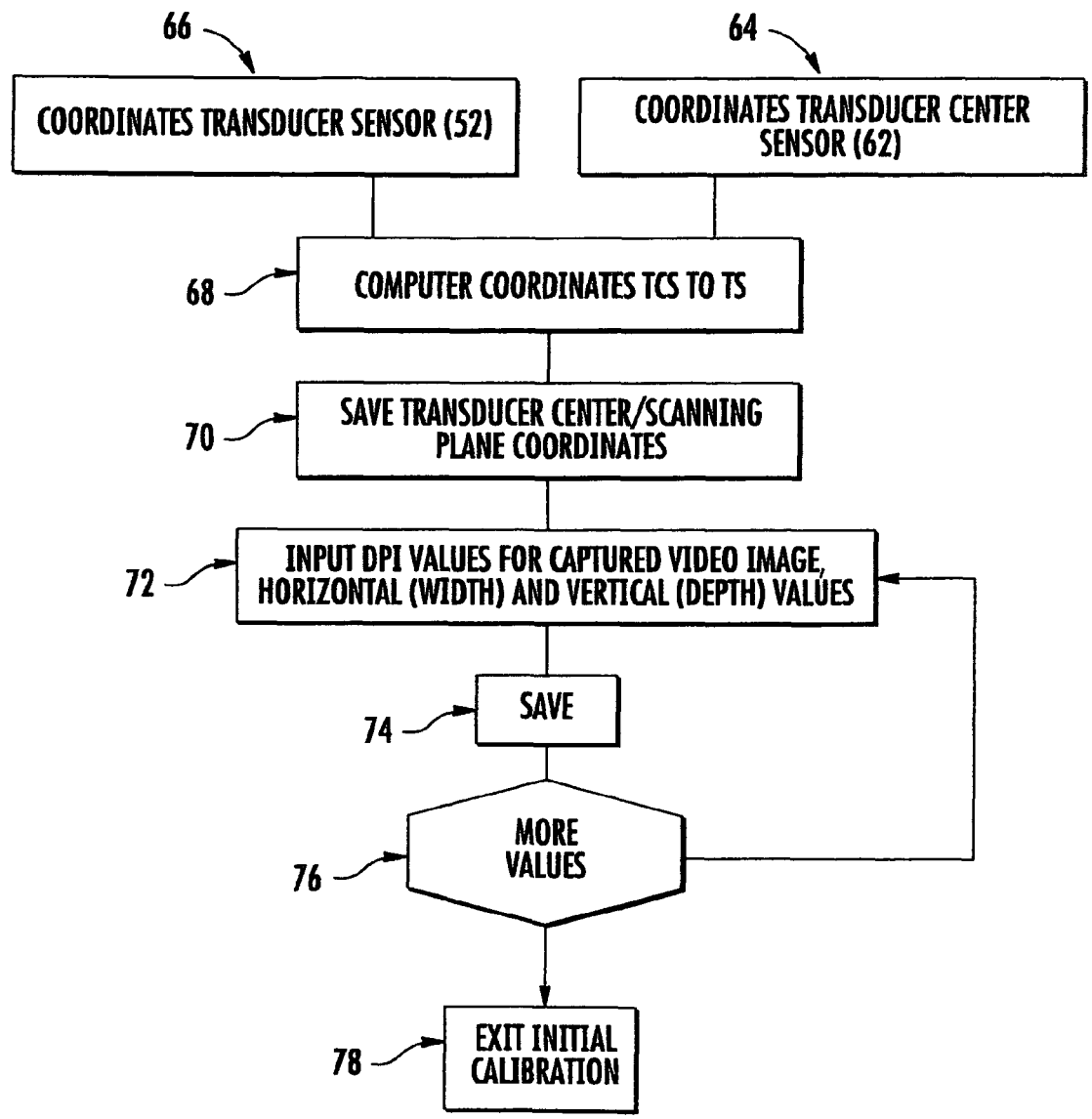
FIG. 8 illustrates the steps of initial calibration.

The initial system calibration steps are shown in FIG. 8. When performing the second magnetic sensor 52 calibration, TDMD computer 40 registers the 3D position of sensor 52 in relation to the center of the transducer 34 scanning head 64 and in relation to the transducer scanning plane 68, so it can accurately define the position of each pixel in the ultrasound image in relation to the transducer scanning head and first magnetic sensor 48. That coordinate is then saved 70. In addition to the above sensor initial calibration, the ultrasound image size calibration is needed for each transducer 72, in dots per inch (dpi) or per mm and it can be done automatically in systems where this information is passed from the ultrasound machine, 22, to the TDMD computer. For systems where this is not possible, the manual calibration for image size: depth and width, is needed and can be performed by manually entering the calculated values, obtained by dividing the number of pixels to the size of markers of known size in the ultrasound image. This information is then saved 74. The process is repeated 76 until all required values are calculated and saved 76. The initial calibration process is then exited 78.

Figure 9:
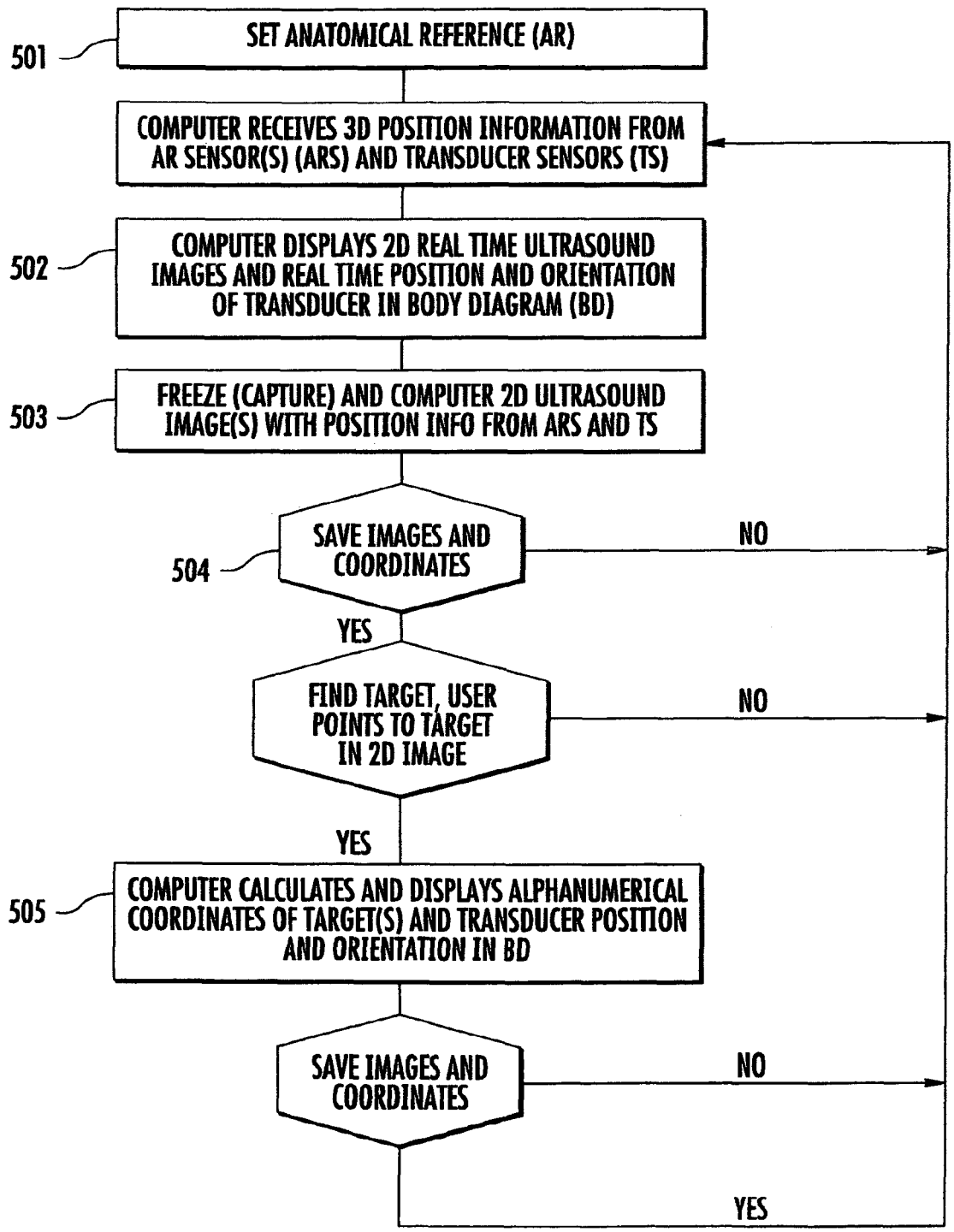
FIG. 9 illustrates the steps needed to measure and record the positional information associated with the diagnostic ultrasound images.

Turning to FIG. 9, the TDMD operation steps required to record the 3D position of targets in relation to anatomical reference points are shown. For each patient, at the beginning of examination the anatomical reference spatial position and the ultrasound probe orientation relative to the body is defined and recorded, 501. One method is to hold the ultrasound transducer scanhead center at the anatomical reference, for ex. on the nipple, with the transducer held in the preset orientation, ex. sagital plane, horizontal, parallel to the patient and examination table long axis (FIG. 1). At least one anatomical reference point needs to be defined at the beginning of each examination, however more than one anatomical reference points can be defined, which can increase the measurements accuracy. When a second magnetic sensor is used to track the anatomical reference position, the first magnetic sensor 48 position in relation to the anatomical reference point is recorded and computed by the TDMD 40 during the anatomical reference setting step, so it can continuously track the anatomical reference point. This additional calculation is necessary when the first magnetic sensor 48 is applied in close proximity, but slightly off the selected anatomical reference. In other embodiments where the anatomical reference sensor or marker, for example when using the overhead anatomical reference tracking system with infrared reflectors or markers or optical markers, is applied exactly at the anatomical reference point, this additional correction is not necessary and can be skipped. If the magnetic anatomical reference marker can be applied exactly at the anatomical reference point, this additional correction is not necessary and can be skipped.

Continuing with FIG. 8, at 502 the transducer 34 position and orientation and anatomical reference point are continuously displayed in TDMD computer display 38 or ultrasound display 24, as a moving icon over the body part diagram, in reference to the anatomical reference point, with an "out of range" warning when the transducer is moved out of the scanning region range or too far from the magnetic transmitter. The frame images are entered and displayed in the TDMD display 38 or if implemented at the ultrasound machine host computer, ultrasound display 24. In the preferred embodiment, the ultrasound user can "freeze" the 2D still image of interest or capture short video cine loops or 3D images, 503 (FIG. 8). The "frozen" image or the video clip can be saved in TDMD computer 40 or a host computer with the positional information associated to each frame or set of frame images, in a local database, 504, (FIG. 9).

The coordinates associated with a target in a still image, in relation to the anatomical reference point, can be displayed by pointing to the target (image pixel/region of pixels) with a pointing device in the image displayed on the TDMD display 38 or Ultrasound display 24, step 505 (FIG. 9). The target position can be also determined at a later time in the same TDMD computer or a remote computer with the TDMD software, from the saved ultrasound images with the associated positional information. The target positional information can be displayed at the time of the ultrasound examination or at a later date, it also can be printed and stored in digital format at any time after the acquisition.

For the images in cine loops, the position display process is similar to the still images, after the cine loop is "frozen" at a certain frame. For 3D ultrasound probes, the same principle applies when a 2D image is reconstructed from the recorded 3D data and the positioning information is applied to the ultrasound 2D image.

The position of each pixel in an ultrasound image in reference to the anatomical reference(s) is calculated from the ultrasound probe tracking system data and corrections applied to the anatomical reference points from the secondary tracking system that monitors the anatomical reference points. Both tracking systems provide 3D positional data. The positional information displayed for each image is presented in alphanumerical format as distance and angle from the anatomical reference, hourly coordinates, where the position of a target is assigned an hour from 1 to 12 o'clock, when the region (breast or abdomen) is viewed from above as a clock, with the anatomical reference, nipple or umbilicus respectively, imagined in the middle of the clock and also as a graphic diagram of the region, see, e.g., FIG. 6. Additional data fields are also available, including the position of the patient during the examination (supine, lateral decubitus, etc). The graphic diagram points to the relative position of a target over a diagram of a body part, the breast, for example. Accordingly, it is easy to see that multiple targets can be selected/displayed or erased.

The TDMD computer allows for the manual or automatic entry and display of target coordinates from previous exams over the body diagram or body part diagram, with the ultrasound probe icon position and orientation in relation to the anatomical reference point and body axis, represented in real time in the diagram. This feature allows for ultrasound device operator orientation and guidance to help moving the ultrasound transducer and find a known target from a previous examination.

Accordingly, the present invention is a system and method where a target position in a human or animal body can be automatically recorded in reference to any preset anatomical reference point, when performing an ultrasound examination. The system allows for automatic correction for body or anatomical reference motion during the examination.

It is to be understood that while the invention has been described as being implemented on the ultrasound machine itself, it is capable of other deployments as well. For non-limiting example, it could be deployed at the level of a host computer or a separate computer from the ultrasound system where the separate computer is connected to the ultrasound machine so it can simultaneously display the image outputs from the ultrasound machine and the diagnostic image positional information in graphic and alpha-numeric modes from the TDMD device. The information from the separate computer can be stored as hardcopy or it can be digitally stored.

It is also to be understood, that even though numerous characteristics and advantages of the preferred and alternative embodiments have been set forth in the foregoing description, together with details of the structure and function of the embodiments, the disclosure is illustrative only, and changes may be made in detail within the principles of the invention to the full extent indicated by the broad general meaning of the terms in which the appended claims are expressed.

I claim:

1. An ultrasound image registration system comprising:
   an ultrasound imaging probe configured to acquire ultrasound image data during an examination, the image data calibrated to the ultrasound imaging probe;
   an imaging probe sensor coupled to the ultrasound imaging probe, the imaging probe sensor comprising a magnetic sensor configured to track a realtime position and a realtime orientation of the ultrasound imaging probe;
   an anatomical reference sensor coupleable to a patient body and configured to track a realtime position of an anatomical reference point on the patient body during the examination; and
   a processor programmed to:
      detect and record an orientation of a body axis of the patient body relative to the ultrasound imaging probe;
      continuously track the realtime position of the anatomical reference point by monitoring a location of the anatomical reference sensor during the examination;
      continuously track the realtime position of the ultrasound imaging probe relative to the realtime position of the anatomical reference point by monitoring the imaging probe sensor and the anatomical reference sensor during the examination;
      continuously track the realtime orientation of the ultrasound imaging probe relative to the detected body axis by monitoring the ultrasound imaging probe sensor during the examination;

calculate a position of a body target in a captured ultrasound image generated from the acquired image data relative to the anatomical reference point and the detected body axis;

simultaneously display as overlays on a graphic diagram of the patient body during the examination (A) the realtime position of the ultrasound imaging probe, (B) the realtime orientation of the ultrasound imaging probe, (C) the realtime position of the anatomical reference point, and (D) the position of the target;

wherein the realtime position of the anatomical reference point is tracked independent from the orientation of the detected body axis.

2. The image registration system of claim 1 wherein the processor is further programmed to display the position of the body target in an alphanumerical format alongside the graphic diagram as:

a distance from the anatomical reference point; and a position relative to the detected body axis centered on the anatomical reference point, displayed in one of (A) degrees and (B) hours and minutes.

3. The image registration system of claim 1 wherein the graphic diagram of the patient body comprises a two-dimensional representation of a region of the patient body.

4. The image registration system of claim 1 wherein the processor is further programmed to calculate a three-dimensional position of the body target relative to the anatomical reference point and the detected body axis.

5. The image registration system of claim 1 wherein the processor is further programmed to:

display the captured ultrasound image alongside the graphic diagram of the patient body; and display a marked location of the body target as an overlay on the captured ultrasound image.

6. The image registration system of claim 1 wherein the processor is further programmed to register the position of the ultrasound imaging probe relative to the sagital plane of the patient body.

7. The image registration system of claim 1 wherein the ultrasound imaging probe comprises a three-dimensional (3D) ultrasound probe.

8. The image registration system of claim 1 wherein the processor is further programmed to simultaneously:

display the position of the body target in reference to the anatomical reference point in a body orientation coordinate system comprising hours and minutes, with the anatomical reference point positioned in the center of the body orientation coordinate system; and display a depth of the body target relative to the anatomical reference point.

9. The image registration system of claim 1 wherein the processor is further programmed to display the location of the ultrasound imaging probe as a moving icon on the graphic diagram of the patient body.

10. The image registration system of claim 1 wherein the graphic diagram of the patient body comprises a three-dimensional representation of a body region of the patient.

11. The image registration system of claim 1 wherein the anatomical reference sensor is coupleable to a breast nipple of the patient and is configured to identify a realtime location of the breast nipple during the examination.

12. The image registration system of claim 1 wherein the processor is further programmed to display the position and orientation of the ultrasound imaging probe as a distance from the anatomical reference point relative to the orientation of the patient body.

13. A method comprising:

defining a position of an anatomical reference point on a breast of a patient relative to an ultrasound imaging probe of an ultrasound imaging system, the anatomical reference point corresponding to a breast nipple;

identifying a orientation of the ultrasound imaging probe relative to a body axis of the patient at the beginning of an examination;

acquiring image data from the patient using the ultrasound imaging probe during the examination, the image data calibrated to the ultrasound imaging probe;

tracking a realtime position of the anatomical reference point during the examination using a first magnetic sensor coupleable to the breast;

tracking a realtime position and a realtime orientation of the ultrasound imaging probe during the examination using a second magnetic sensor coupled to the ultrasound imaging probe;

reconstructing an image of the patient from the image data, the image comprising a plurality of pixels;

calculating a spatial position of each of the plurality of pixels in the image in reference to the anatomical reference point;

calculating an angular position of each of the plurality of pixels in the image in reference to the body axis of the patient and the anatomical reference point;

identifying a breast target within the image, the breast target corresponding to a specific location within the breast; and simultaneously displaying on a display:

the image having the body target identified therein;

a graphic diagram of the breast having the realtime position of the ultrasound imaging probe, the realtime orientation of the ultrasound imaging probe, and the realtime position of the anatomical reference point identified therein;

coordinates of the breast target relative to the realtime position of the anatomical reference point; and coordinates of the breast target relative to the body axis of the patient.

14. The method of claim 13 further comprising continuously displaying the realtime position of the anatomical reference point, the realtime position of the ultrasound imaging probe, and the realtime orientation of the ultrasound imaging probe during acquisition of image data on the display.

15. The method of claim 13 further comprising displaying coordinates of the breast target in a body orientation coordinate system comprising hours and minutes on the display, wherein the coordinates represent the position of the breast target in reference to the anatomical reference point, with the anatomical reference point defined as the center of the body orientation coordinate system.

16. The method of claim 15 further comprising displaying a depth of the breast target relative to the anatomical reference point on the display.

* * * * *